United States Patent [19]

Dixon

[11] 4,112,010
[45] Sep. 5, 1978

[54] PARALLEL ALKYLATION ZONES WITH ALKYLATE PRODUCT AND PROPANE REMOVAL FROM A FLASH ZONE AND A FRACTIONATION ZONE

[75] Inventor: Rolland E. Dixon, Bartlesville, Okla.

[73] Assignee: Phillips Petroleum Company, Bartlesville, Okla.

[21] Appl. No.: 800,388

[22] Filed: May 25, 1977

[51] Int. Cl.² ............................................. C07C 3/54
[52] U.S. Cl. ............................................. 260/683.48
[58] Field of Search .................. 260/683.48, 683.45, 260/683.46

[56] References Cited

U.S. PATENT DOCUMENTS

| | | | |
|---|---|---|---|
| 2,820,073 | 1/1958 | Dixon et al. | 260/683.45 |
| 3,007,982 | 11/1961 | Clauson | 260/683.46 |
| 3,007,983 | 11/1961 | Clauson | 260/683.46 |

*Primary Examiner*—George Crasanakis

[57] ABSTRACT

In a dual alkylation system, the hydrocarbon phase from one settling zone is flash distilled to provide the isoparaffin for a second alkylation reactor, resulting in considerable energy savings, yet producing a high quality alkylate.

8 Claims, 1 Drawing Figure

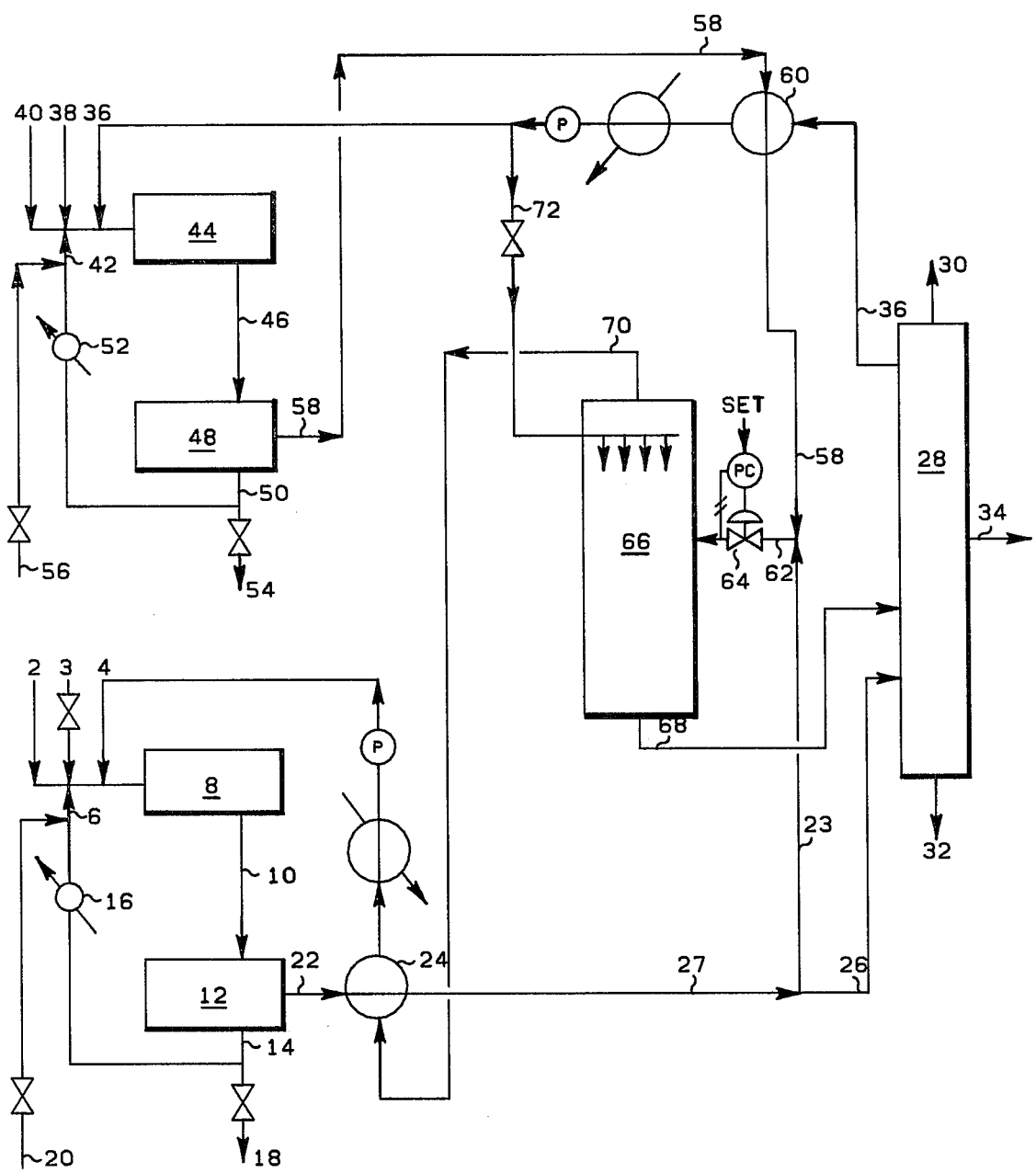

PARALLEL ALKYLATION ZONES WITH ALKYLATE PRODUCT AND PROPANE REMOVAL FROM A FLASH ZONE AND A FRACTIONATION ZONE

The present invention relates to the alkylation of hydrocarbons.

The alkylation of an isoparaffin, such as isobutane, isopentane, and the like, with one or more olefins, such as propylene, butylenes, amylenes, and the like, is well known as a commercially important method for producing gasoline boiling range hydrocarbons. The $C_5$ to $C_{10}$ hydrocarbons generally produced by the alkylation reaction are termed "alkylate". Alkylate is particularly useful as a motor fuel blending stock because of its high octane ratings.

Various types of catalysts have been used in the alkylation reaction, including sulfuric acid, hydrochloric acid, phosphoric acid, certain halosulfonic acids and aluminum chloride. The preferred catalyst is substantially anhydrous hydrofluoric acid because of the relative ease with which it can be used and reused and because of the superior quality of the alkylate that is produced. It is the usual practice to alkylate an isoparaffin with two different olefins in separate reactors and to pass the individual alkylate-containing streams to separate separation zones. It is also known to alkylate an isoparaffin with two different olefins in separate alkylators and pass the individual alkylate streams to a common settler provided with a partition spaced from the top and bottom of the separator, thereby allowing communication between the separate sections of the settler. Also, in this latter system the acid catalyst is combined and returned as a single stream to the respective alkylators.

Isoparaffin-olefin alkylation processes are generally conducted at particular conditions of temperature and pressure, and at specific concentrations of reactants and catalysts in order to produce an optimum yield of high quality alkylate product. A large molar excess of isoparaffin, relative to the olefin, in the reaction mixture, generally 10:1 to 30:1, is one of the necessary conditions since the quality of the alkylate product is generally improved by such large excess of isoparaffin. Thus, a considerable quantity of isoparaffin is generally recovered and recycled to the reactor after separation from the hydrocarbon phase of the reactor effluent. The large amount of isoparaffin which must be passed, unreacted, through the alkylation reactor and settler requires the use of fractionation equipment of large capacity in order to provide adequate separation of the product alkylate from the isoparaffin to be recycled. Such large capacity fractionation equipment is expensive to construct and requires large quantities of energy. It is desirable to fractionate a product resulting from the reaction of an isoparaffin, olefins and an acid catalyst while maintaining the size and energy requirements for such fractionation at a low level, particularly where energy is valuable and the products for generating the energy are in relatively short supply.

The present invention, therefore, resides in an improved alkylation process wherein an isoparaffin is separately alkylated in two alkylation reactors, which allows dual use of the large volume of isoparaffin recycle in the two successive reactor stages with minimal, low cost separation to recover isoparaffin and the major portion of the alkylate produced in one of the reactor stages.

Accordingly, it is an object of the present invention to provide an improved alkylation process.

Other objects, aspects and advantages of the present invention will become apparent from a study of the disclosure, the appended claims and the drawing.

In accordance with the present invention, there is provided a process which comprises alkylating in separate alkylation reactors an isoparaffin with at least one olefin, preferably different olefins, under alkylation conditions using a liquid acid alkylation catalyst, separately recovering the hydrocarbon reaction mixtures from the acid catalyst, subjecting the reaction mixture from one alkylation stage to flash distillation to separate the excess isoparaffin and the alkylate and passing the flashed isoparaffin to the second alkylation reactor. The alkylate obtained from the flash distillation and at least a portion of the reaction mixture from the second stage are fractionated to obtain an alkylate product.

The process of this invention can be employed to alkylate an isoparaffin with different olefins or to separately alkylate an isoparaffin with one olefin or a mixture of olefins.

The preferred olefins in the process are propylene and butenes, but any $C_3$ to $C_7$ olefins can be used. Isobutane is preferred as the isoparaffin, but $C_5$ to $C_8$ isoparaffins can also be used, depending on the alkylate desired.

The alkylation temperature can range from about 40° to 200° F; however, when alkylating isobutane with a butene or mixture of butenes, using a hydrogen fluoride catalyst, a reaction temperature in the approximate range of 60° to 95° F is now preferred, and when alkylating isobutane with propylene, using HF catalyst, a temperature in the approximate range of 100° to 125° F is now preferred.

The alkylation pressure is at least sufficient to maintain the reactants and products in the liquid phase in the alkylation reactors and settlers.

The mol ratio of isoparaffin to olefin is generally maintained in the range of 6:1 to 30:1, preferably above 10:1. The volume ratio of acid to hydrocarbon feed, particularly when using hydrofluoric acid, is maintained at about 0.5:1 to 6:1, preferably about 4:1.

The invention encompasses the use of different isoparaffins as well as different olefins in the feeds to the alkylation reactors. Thus, isobutane can be fed to one alkylator e.g. to react with butylenes while isopentane is fed to the other alkylator e.g. to react with propylene.

A better understanding of the invention will be obtained by reference to the accompanying drawing which shows an arrangement of apparatus representing the preferred embodiment of the invention.

Referring now to the drawing, propylene, the lighter olefin, and recycle isobutane, recovered as hereinafter described, are charged along with liquid hydrofluoric acid catalyst by way of lines 2, 4 and 6, respectively, to HF alkylation zone 8, wherein the isobutane is alkylated with the propylene to produce gasoline alkylate. Additional isobutane may be charged to alkylation zone 8 through line 3, as required to increase the isobutane to propylene ratio.

The mixture of hydrocarbon and HF catalyst from alkylation zone 8 is passed by way of line 10 to phase separation zone 12, wherefrom settled catalyst is removed by way of line 14, cooled by indirect heat exchange in cooler 16 and recycled to alkylation zone 8 through line 6. A portion of the catalyst can be removed by way of line 18 and charged to conventional HF rerun facilities, not shown. Rerun HF and make-up HF can be added back to the alkylation system through line 20.

The first reaction mixture, i.e., hydrocarbon liquid phase, is withdrawn from separation zone 12 by way of line 22 and is passed in indirect heat heat exchange with the isobutane in line 4 in heat exchanger 24. A portion of the reaction mixture is passed through line 26 to fractionation zone 28 wherein a light stream comprising propane is removed overhead by way of line 30, alkylate bottoms product is removed by way of line 32, a side stream comprising n-butane is removed by way of line 34 and an upper cut comprising isobutane is removed by way of line 36.

The recycle isobutane 36, feed isobutane 38 and bu-tenes 40 are charged along with liquid HF catalyst 42, to a second HF alkylation zone 44, wherein the isobutane is alkylated with the butenes to produce gasoline alkylate. The mixture of hydrocarbon and HF catalyst from alkylation zone 44 is passed by way of line 46 to phase separation zone 48, wherefrom settled catalyst is removed by way of line 50, cooled by indirect heat exchange in cooler 52 and recycled to alkylation zone 44 through line 42. A portion of the catalyst can be removed by way of line 54 and charged to conventional HF rerun facilities, not shown. Rerun HF and make-up HF can be added back to the alkylation system through line 56.

The second reaction mixture is withdrawn from the second separation zone 48 by way of line 58 and is passed in indirect heat exchange with the isobutane in line 36 in heat exchanger 60. The remaining portion of the first reaction mixture is passed by way of line 23 and combined with the second reaction mixture in line 58 and the resulting combined stream is passed by way of line 62, which has pressure control valve 64 thereon, to flash zone 66. After passing pressure control valve 64, the pressure is so reduced on the combined reaction mixture as to refrigerate it and vaporize the volatile hydrocarbons, mainly isobutane. The alkylate therein is essentially non-vaporizable under the pressures and temperatures existing in this system. The majority (or all) of the alkylate is withdrawn as bottoms from flash zone 66 and passed by way of line 68 to fractionation zone 28. The flashed volatile hydrocarbons are withdrawn overhead from flash zone 66 and passed by way of line 70 to heat exchanger 24, then, after indirect heat exchange with the first reaction mixture are passed by way of line 4 to the first alkylation zone 8.

There may be a small amount of alkylate carryover in the flashed isobutane recycle line 70. If desired, liquid isobutane can be withdrawn from the fractionator isobutane recycle line 36 and passed by way of line 72 to flash zone 66 as reflux.

It is apparent that the drawing is somewhat simplified in that many parts such as valves, pumps, heaters, coolers, condensers, and other conventional equipment are not shown. However, their inclusion is understood by those skilled in the art and is within the scope of this invention.

The reaction zones can comprise any alkylation reactor known in the art. A preferred type is a simple pipe or conduit riser-reactor, as shown in U.S. Pat. No. 3,213,157.

The settling zones can comprise any type of vessel known in the art for achieving phase separation, such as the vessel shown in U.S. Pat. No. 3,213,157.

The flash zone can be a conventional flash drum.

EXAMPLE

The following calculated example illustrates the invention:

| Stream No. | 40 | 38 | 36 | 58 | 2 | 4 | 22 | 23 | 26 | 68 | 32 | 34 | 30 |
|---|---|---|---|---|---|---|---|---|---|---|---|---|---|
| Composition | | | | | Fluid Flow, Barrels per Day | | | | | | | | |
| Propylene | — | — | — | — | 2,920 | — | — | — | — | — | — | — | — |
| Propane | — | — | 2,897 | 2,897 | 1,080 | 7,584 | 9,014 | 5,590 | 3,424 | 903 | — | — | 1,430 |
| Isobutane | 1,538 | 4,726 | 42,648 | 46,467 | — | 70,080 | 66,311 | 41,121 | 25,190 | 17,508 | — | 50 | — |
| Normal Butane | 500 | 249 | 5,017 | 5,766 | — | 8,691 | 8,691 | 5,390 | 3,301 | 2,465 | — | 749 | — |
| Butylenes | 2,038 | — | — | — | — | — | — | — | — | — | — | — | — |
| Alkylate | — | — | — | 3,607 | — | 109 | 5,131 | 3,182 | 1,949 | 6,680 | 8,629 | — | — |
| Total | 4,076 | 4,975 | 50,562 | 58,737 | 4,000 | 86,464 | 89,147 | 55,283 | 33,864 | 27,556 | 8,629 | 799 | 1,430 |

| Operating Conditions: | |
|---|---|
| Alkylation Reactor 44: | |
| Temperature, °F | 85° F (29.4° C) |
| Pressure | to maintain liquid phase |
| Isobutane-butenes, mol ratio | about 24 |
| HF:hydrocarbon, volume ratio | about 4 |
| Alkylation Reactor 8: | |
| Temperature | 110° F (43.3° C) |
| Pressure | to maintain liquid phase |
| Isobutane:propylene, mol ratio | about 24 |
| HF-hydrocarbon, volume ratio | about 4 |
| Flash zone 66: | |
| Temperature | 140° F (60° C) |
| Pressure | 85 psig (586.5 kPa) |
| Fractionation zone 28: | |
| Top temperature | 150° F (65.6° C) |
| Bottom temperature | 310° F (154.4° C) |
| Pressure | 185 psig (1276.5 kPa) |

Reasonable variations and modifications, which will be apparent to those skilled in the art, can be made in this invention without departing from the spirit and scope thereof.

What is claimed is:

1. A process for simultaneously and separately alkylating a first stream consisting essentially of an isoparaffin and propylene and a second stream consisting essentially of an isoparaffin and at least one olefin having from 4 to 7 carbon atoms which comprises
   passing said first stream in admixture with a first portion of an acid alkylation catalyst through a first alkylation zone under alkylation conditions to form a first reaction mixture,
   simultaneously passing said second stream in admixture with a second portion of said catalyst through a second alkylation zone under alkylation conditions to form a second reaction mixture,
   passing said first reaction mixture to a first settling zone wherein said first reaction mixture separates into a first hydrocarbon phase and a first catalyst phase,
   passing said second mixture is a second settling zone wherein said second mixture separates into a second hydrocarbon phase and a second catalyst phase,
withdrawing said first catalyst phase from said first settling zone,
withdrawing said second catalyst phase from said second settling zone,
withdrawing said first hydrocarbon phase from said first settling zone,
withdrawing said second hydrocarbon phase from said second settling zone,
dividing said first hydrocarbon phase into a first portion in an amount based on the propane to be removed from the process and a second portion,
passing said first portion of said first hydrocarbon phase to a fractionation zone,
removing said propane from said fractionation zone,
removing isoparaffin from said fractionation zone,
passing at least a major portion of said isoparaffin as recycle to said second alkylation zone,
combining said second hydrocarbon phase with said second portion of said first hydrocarbon phase,
passing the resulting combined hydrocarbon stream to a flash zone for separation therein of said combined stream into an isoparaffin-rich overhead stream and an alkylate-rich bottoms stream,
withdrawing said alkylate-rich bottoms stream from said flash zone,
passing said alkylate-rich bottoms stream to said fractionation zone,
withdrawing said isoparaffin-rich overhead stream from said flash zone,
passing said isoparaffin-rich overhead stream to said first alkylation zone, and
withdrawing an alkylate product stream from said fractionation zone.

2. A process according to claim 1 wherein said second hydrocarbon phase is passed in indirect heat exchange with said isoparaffin recycle stream prior to combining said second hydrocarbon phase with said second portion of said first hydrocarbon phase.

3. A process according to claim 1 wherein said isoparaffin-rich overhead stream is passed in indirect heat exchange with said first hydrocarbon phase prior to passing of said isoparaffin-rich overhead stream to said first alkylation zone.

4. A process according to claim 1 wherein said isoparaffin has from 4 to 8 carbon atoms per molecule.

5. A process according to claim 1 wherein said isoparaffin is isobutane and said olefin employed in said second stream is butene.

6. A process according to claim 1 wherein the ratio of isoparaffin to olefin in said alkylation zones is in the approximate range of 6:1 to 30:1.

7. A process according to claim 1 wherein said alkylation reaction is carried out in the liquid phase at a temperature in the approximate range of 40° to 200° F.

8. A process according to claim 1 wherein said catalyst is liquid hydrofluoric acid.

* * * * *